(12) United States Patent
McPherson et al.

(10) Patent No.: US 6,203,811 B1
(45) Date of Patent: Mar. 20, 2001

(54) TERMITE CONTROL COMPOSITIONS

(75) Inventors: Brice A. McPherson, Oakland; David L. Wood, Moraga, both of CA (US)

(73) Assignee: The Regents of the University of California, Berkeley, CA (US)

( * ) Notice: Subject to any disclaimer, the term of this patent is extended or adjusted under 35 U.S.C. 154(b) by 0 days.

(21) Appl. No.: 09/313,126

(22) Filed: May 17, 1999

Related U.S. Application Data (60) Provisional application No. 60/086,154, filed on May 19, 1998.
(51) Int. Cl.[7] .......................... A01N 25/00; A01N 25/08; A01N 63/00; A01N 63/04; C12N 1/14
(52) U.S. Cl. .................. 424/405; 424/410; 424/93.5; 424/115; 435/254.1; 435/256.2; 435/256.6
(58) Field of Search ................................. 424/405, 410, 424/93.5, 115; 435/254.1, 256.2

(56) References Cited

PUBLICATIONS

Amburgery, Terry L., "Review and Checklist of the Literature on Interactions Between Wood–Inhabiting Fungi and Subterranean Termites: 1960–1978", 1979, Sociobiology, vol. 4, No. 2, pp. 279–296.

Amburgery, T. L., et al., "Factors Influencing Termite Feeding on Brown–rotted Wood", 1977, pp. 2–12. Sociobiology, vol. 3, No. 1.

Bernays, E.A, et al., "Host–Plant Selection By Phytophagous Insects", Chapman & Hall, New York, London, pp. 59–94. Contemporary Topics in Entomology 2.

Esenther, G. R., "Termite Attractant from Fungus–Infected Wood", Mar. 1961, Department of Entomolgy, University of Wisconsin, Science, vol. 134, p. 50.

Grace, Kenneth J., "A Simple Humidity Chamber for Maintaining Subterranean Termites (Isoptera: Rhinotermitidae) in the Laboratory", 1986, Pan–Pacific Entomologist, vol. 62, No. 3, pp. 221–223.

Grace, Kenneth J., et al., Isolation and Trail–Following Bioassay of a Decay Fungus Associated with *Reticulitermes hesperus* Banks (Isoptera: Rhinotermitidae), 1988, Pan–Pacific Entomologist, pp. 243–249. vol. 64, No. 3.

Hendee, Esther, "The Role of Fungi in the Diet of Termites", vol. 80, No. 2075, p. 316. Science, 1935.

Kovoor, Jacqueline, "Modifications Chimiques Provoquées Par Un Termitidé (Microrotermes Edentatus, Was.) Dans Du Bois De Peuplier Sain Ou Partiellement Dégradé Par Des Champignons", 1964, Laborotoire d'Evolution des Êtres organisés, pp. 491–510.

Matsumura, F., et al., "Termited Trail–Following Substance, Isolation and Purification from Reticulitermes virginicus and Fungus–Infected Wood", Jun. 1969, Department of Entomology, University of Wisconsin, pp. 599–603. J. of Economic Entomology.

Matsuo, Haruo, et al., "Response of the Termite Coptotermes formosannus (Shiraki) to Extract Fractions from Fungus–infected Wood and Fungus Mycelium", 1974, Wood Research Institute, Kyoto University, pp. 225–238.

Moein, Samia I., et al., The Effect of Wood Degradation by Fungi on the Feeding and Survival of the West Indian Drywood Termite, *Cryptotermes brevis* (Isoptera: Kalotermitidae), 1992, Sabahia Research Station, Alexandria, vol. 20, No. 1, pp. 28–39. Sociobiology.

Sands, William A., "The Association of Termites and Fungi", 1969, vol. I, Academic Press, New York and London, pp. 495–524.

Hendee, University of California Publications in Zoology, vol. 39, pp. 111–133, 1933.*

Rust et al. Sociobiology, vol. 28, pp. 275–286, 1996.*

Zoberi et al. Mycologia, vol. 82, No. 3, pp. 289–294, 1990.*

Becker, G. "Termites and fungi." Material und Organismen Beiheft, vol. 3, pp. 465–478, 1976.* van Arx, J. A. "On Nucoracea s. str. and other familes of the Mucorales." Sydowia, vol. 35, pp. 10–26, 1982.*

* cited by examiner

Primary Examiner—Francisco Prats
Assistant Examiner—Susan D. Coe
(74) Attorney, Agent, or Firm—Beyer Weaver & Thomas, LLP (57) ABSTRACT

Provided are termite phagostimulatory compositions extracted from fungi coexisting with subterranean termites. In a preferred embodiment, a subterranean termite feeding stimulant is obtained from extracts of fungi coexisting with *Reticulitermes hesperus*. Termite feeding stimulants in accordance with the present invention may be incorporated into termiticide-treated bait-based systems and methods to selectively target and enhance control of subterranean termites. Also provided are compositions which deter feeding of subterranean termites. These phagodeterrent compositions may be obtained from non-polar extracts of subterranean termite-associated fungus-colonized filter paper. They may also find useful application in termite control strategies, for example, by deterring subterranean termites from colonizing or feeding on particular substrates and structures.

19 Claims, 4 Drawing Sheets

TERMITE CONTROL COMPOSITIONS

CROSS-REFERENCE TO RELATED APPLICATIONS

This application claims the benefit of the priority date of Provisional Patent Application Ser. No. 60/086,154, filed May 19, 1998, the disclosure of which is incorporated by reference herein for all purposes.

FIELD OF THE INVENTION

This invention relates generally to termites, and in particular to termite feeding stimulants and deterrents, and methods of their use for termite control.

BACKGROUND

Subterranean termites (family Rhinotermitidae) are major decomposers of wood and other cellulosic materials. Since subterranean termites construct their nests not only in soil, but in dead wood, including wooden structures, they are major insect pests. Conventional methods for termite control have focused on the application of toxic synthetic organic chemicals, such as pyrethroids. These chemicals are typically applied as a barrier to prevent entry of termites into wooden structures, and/or directly to termite colonies by drilling into subterranean termite nests. However, the introduction of pesticides into the characteristically extensive colonies of subterranean termites by such conventional means is unreliable. Effective control is difficult to assess, greater amounts of pesticides are likely to be used than are necessary, and the prevention or elimination of a building infestation may not seriously affect the source colony.

Another, more recently applied, subterranean termite control strategy involves the use of poisoned baits. DowElanco (now Dow AgroSciences) has developed a poisoned bait subterranean termite control system called Sentricon™. The Sentricon™ system typically includes several termite colony elimination stations. Each station is composed of a plastic tube (housing) about 4 by 24 cm with a removable top cap. Typically, a number of Sentricon™ stations are inserted into the ground in the region of a subterranean termite colony, and a termiticide-treated bait material is placed in each station housing. The Sentricon™ system uses Dow AgroSciences' Recruit™ II Baitube™ devices containing approximately 30 g of cellulose material impregnated with 0.5% (w/w) hexaflumuron as the bait material. Hexaflumuron acts as an insect growth regulator (IGR), inhibiting the normal molting process of the termites, resulting in death. The success of the Sentricon™ system in eliminating colonies of several species of subterranean termites has been documented.

Research on the chemical basis of food selection for many major agricultural insect pests has led to improved understanding of feeding behaviors. This has in turn suggested improved monitoring and control strategies. An example of this is the corn rootworm, *Diabrotica undecimpunctata,* for which both monitoring and toxic bait techniques have been developed based on knowledge of the chemical basis of food selection. Incorporation of a subterranean termite feeding stimulant into a termiticide-treated bait has the potential to selectively target termite colonies and enhance control of cryptic subterranean termites. Such an approach would also take advantage of the food exchanging behavior (trophallaxis) characteristic of subterranean termites. However, very little is known about the chemical and environmental cues used in food selection by subterranean termites, and compositions which stimulate feeding of subterranean termites have not previously been identified.

The widespread observation that termites coexist with fungi in dead wood suggests that fungi enhance the wood's value for the termites (Hendee, E. C. (1934). *The Role of Fungi in the Diet of Termites.* Science 80(2075): 316; Kovoor, J. (1964). *Modifications chimiques provoques par un termitidae (Microtermes edentalus, Was.) dans du bois de peuplier sain ou partiellement degrade par des champignons.* Bull. Biol. Fr. Belg. 98: 491–510). Wood structures infested with subterranean termites characteristically also exhibit some fungal presence in close proximity to the termites (Hendee, E. C. (1933). *The Association of the Termites, Kalotermes minor, Reticulitermes hesperus, and Zootermopsis angusticollis with Fungi.* University of California Publications in Zoology 39: 111–133). In field settings, termites are never found without numerous intimately associated fungi, although due to the abundance of fungi in these habitats, this is expected. Since fungi are ubiquitous in soils and dead wood in forested areas, these organisms clearly coexist with subterranean termites in soils and wood. Among the possible influences of fungi on termite ecology are induction of trail-following, directed foraging, and feeding stimulation. For example, fungi may modify the chemical composition of wood as their mycelia penetrate and digest it, incorporating nitrogen and other nutrients into this material, partially pre-digest complex polymeric compounds, or degrade toxic and repellent constituents, any of which could lead to increased feeding and survival of termites.

Both field observations and laboratory experiments with fungal extracts indicate that termite behaviors can be affected by compounds produced by certain fungal species (Esenther, G. R., T. C. Allen, et al. (1961). *Termite attractant from fungus-infected wood.* Science 134(3471): 50; Watanabe, T. and J. E. Casida (1963). *Response of Reticulitermes flavipes to fractions from fungus-infected wood and synthetic chemicals.* Journal of Economic Entomology 56: 300–307). For example, certain basidiomycete fungi are known to produce substances that elicit trail-following in Rhinotermitidae in laboratory assays; i.e., *Gloeophyllum trabeum* (Matsumura, F., Tai, A., & Coppel, H. C. (1969). *Termite Trail-Following Substance, Isolation, and Purification from Reticulitermes virginicus and Fungus-Infected Wood.* Journal of Economic Entomology 62: 599–603; Amburgey, T. and R. V. Smythe (1977a). *Factors influencing termite feeding on brown-rotted wood.* Sociobiology 3(1): 3–12), Oligoporous balsameus (Grace, J. K. and W. W. Wilcox (1988). *Isolation and trail-following bioassay of a decay fungus associated with Reticulitermes hesperus Banks.* Pan-Pacific Entomologist 64(3): 243–249) and *Serpula lacrimans* (among others) (Matsuo, H. and K. Nishimoto (1975). *Response of the Termite Coptotermes formosanus (Shiraki) to Extracts Fractions from Fungus-infected Wood and Fungus Mycelium.* Matererial und Organismen 9: 225–238), although any possible ecological consequences of fungal synthesis of the termite trail-following substances are unknown, and this discovery has not been successfully exploited for termite control. Deleterious effects of fungal extracts on termite feeding and survival have also been shown (Kovoor 1964; Sands, W. A. (1969). *The Association of Termites and Fungi.* Biology of Termites. K. &. W. Krishna F. A. New York, Academic Press. I: 495–524; Matsuo and Nishimoto 1975; Moein, S. I. and M. K. Rust (1992). *The Effect of Wood Degradation by Fungi on the Feeding and Survival of the West Indian Drywood Termite, Cryptotermes brevis (Isoptera: Kalotermitidae).* Sociobiology 20: 29–39). However, despite numerous studies of subterranean termites and fungi (Sands 1969; Becker, G. (1976). *Termites and Fungi.* Material und Organismen Beiheft 3: 465–478; Amburgey, T. (1979). *Review and checklist of the literature on interactions between wood-inhabiting fungi and subterranean termites.* Sociobiology 4(2): 279–296), the implications of joint occupancy have never been adequately explained, and no truly phagostimulatory (feeding-stimulating) or phagodeterrent fungal metabolites have been identified.

Accordingly, it would be desirable to isolate a subterranean termite feeding stimulant, and to incorporate such a feeding stimulant into termiticide-treated bait-based systems and methods to selectively target and enhance control of subterranean termites.

SUMMARY OF THE INVENTION

To achieve the foregoing, the present invention provides termite phagostimulatory compositions extracted from fungi coexisting with subterranean termites. In a preferred embodiment, a subterranean termite feeding stimulant is obtained from extracts of fungi coexisting with *Reticulitermes hesperus*. Termite feeding stimulants in accordance with the present invention may be incorporated into termiticide-treated bait-based systems and methods to selectively target and enhance control of subterranean termites.

In one aspect, the invention provides a subterranean termite phagostimulatory compound extracted from filter paper colonized with fungi coexisting with *Reticulitermes hesperus*. The composition is extracted from the filter paper in the methanol fraction of a sequential methylene chloride ($CH_2Cl_2$); 50% methanol (MeOH)/$CH_2Cl_2$; and MeOH extraction.

In another aspect, the invention provides a subterranean termite phagostimulatory compound extracted from malt-agar cultures of a zygomycete fungus identified as *Micromucor ramannianus*, isolated from filter paper colonized with fungi coexisting with *Reticulitermes hesperus*. The composition is obtained from both polar and non-polar fractions extracted by a sequential methylene chloride ($CH_2Cl_2$); 50% methanol (MeOH)/$CH_2Cl_2$; and MeOH extraction of a malt-agar culture.

In still another aspect, the invention provides compositions which deter feeding of subterranean termites. These phagodeterrent compositions may be obtained from non-polar extracts of subterranean termite-associated fungus-colonized filter paper. They may also find useful application in termite control strategies, for example, by deterring subterranean termites from colonizing or feeding on particular substrates and structures.

These and other features and advantages of the present invention will be presented in more detail in the following specification of the invention and the accompanying figures which illustrate by way of example the principles of the invention.

DETAILED DESCRIPTION OF PREFERRED EMBODIMENTS

The present invention will now be described with reference to several preferred embodiments. Important properties and characteristics of the preferred embodiments are illustrated in the structures in the text and in the accompanying drawings. While the invention will be described in conjunction with these preferred embodiments, it should be understood that the invention is not intended to be limited to these preferred embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

The present invention provides termite phagostimulatory compositions extracted from fungi coexisting with subterranean termites. In a preferred embodiment, a subterranean termite feeding stimulant is obtained from extracts of fungi coexisting with *Reticulitermes hesperus*. Termite feeding stimulants in accordance with the present invention may be incorporated in to termiticide-treated bait-based systems and methods to selectively target and enhance control of subterranean termites.

In one aspect, the invention provides a subterranean termite phagostimulatory compound extracted from filter paper colonized with fungi coexisting with *Reticulitermes hesperus*. The composition is extracted from the filter paper in the methanol fraction of a sequential methylene chloride ($CH_2Cl_2$); 50% methanol (MeOH)/$CH_2Cl_2$; and MeOH extraction.

In another aspect, the invention provides a subterranean termite phagostimulatory compound extracted from malt-agar cultures of a zygomycete fungus identified as *Micromucor ramannianus*, isolated from filter paper colonized with fungi coexisting with *Reticulitermes hesperus*. The composition is obtained from both polar and non-polar fractions extracted of a sequential methylene chloride ($CH_2Cl_2$); 50% methanol (MeOH)/$CH_2Cl_2$; and MeOH extraction of a malt-agar culture.

In still another aspect, the invention provides compositions which deter feeding of subterranean termites. These phagodeterrent compositions may be obtained from nonpolar extracts of subterranean termite-associated funguscolonized filter paper. They may also find useful application in termite control strategies, for example, by deterring subterranean termites from colonizing or feeding on particular substrates and structures.

It should be understood that compositions in accordance of the present invention may also be obtained from fungal colonies coexisting with subterranean termites by comparable extraction techniques using other polar and non-polar solvents, and that the invention is not limited to the use of the specific solvents and other parameters used in the preferred embodiments described in the examples below.

EXAMPLES

The following examples provide details concerning the elucidation of termite feeding stimulants in accordance with the present invention. It should be understood the following is representative only, and that the invention is not limited by the details set forth in these examples.

Example 1

Screening of R. hesperus Fungal Affiliate Extracts for Phagostimulatory Activity Collection and Rearing. Subterranean termites (R. hesperus) were collected from fallen wood and other wood structures (fences and woodpiles) and associated soil in Alameda (urban) and Marin (rural) Counties, California. Six colonies from Marin County were collected and reared in the laboratory, over a period of four years. The Alameda County collections represented two colonies, one of which was sampled repeatedly over a three year period. Wood sources that could be identified to genus included Pinus, Quercus, Acacia, and Pseudotsuga. After the wood was broken into small pieces, this material was placed in Berlese funnels and termites were collected on moist paper towels in mason jars. Once in the laboratory, the paper towels were supplemented with Whatman No. 1 filter paper to provide a chemically pure cellulose food source.

Termites were maintained in the laboratory in large plastic humidity chambers (Grace, J. K. (1986). *A simple humidity chamber for maintaining subterranean termites (Isoptera:Rhinotermitidae) in the laboratory.* Pan-Pacific Entomologist 62(3): 221–223) at approximately 90% relative humidity and ambient temperature. Certain colonies of R. hesperus reared by these methods remained vigorous for five or more years. When maintained in the laboratory, the filter paper provided as diet was colonized by various microorganisms, which were evident due to their discoloration of the paper. These organisms were identified as primarily fungi and bacteria, based on their appearance in agar culture. Colonized papers tended to be avoided by termites. Often, suppression of feeding persisted even when no sound paper remained in the rearing chamber.

Figure 1:
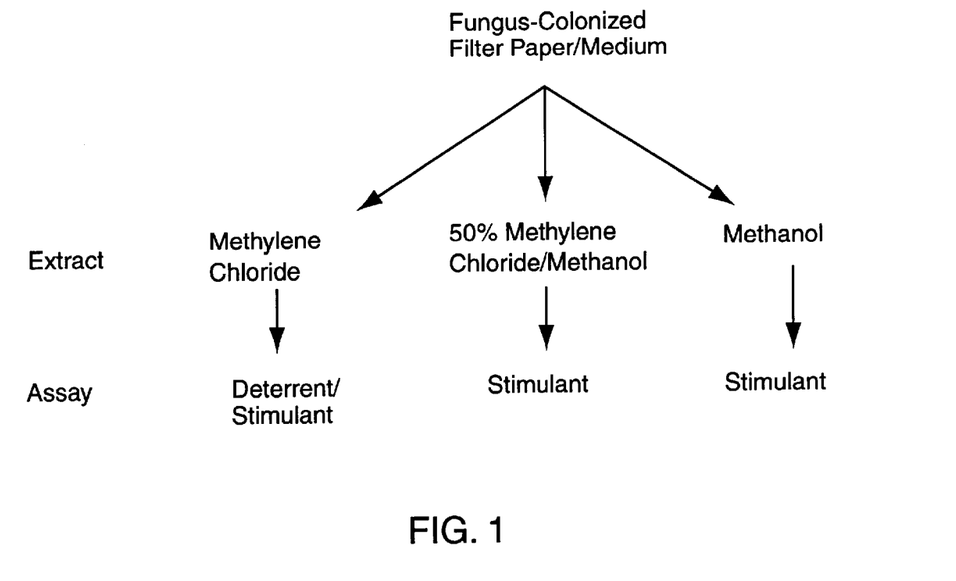
FIG. 1 depicts a process flow diagram illustrating a sequential extraction method for fungal-colonized filter paper and fungal colonies in accordance with a preferred embodiment of the present invention.

Extractions. Colonized filter paper from laboratory colonies representing varied R. hesperus collections was sequentially extracted with solvents of increasing polarity. A portion of the filter paper inhabited by multiple colonies with which feeding avoidance was observed was sequentially extracted with 1) methylene chloride ($CH_2Cl_2$); 2) 50% methanol (MeOH)/$CH_2Cl_2$; and 3) MeOH. The colonized filter paper was extracted in 500 to 800 mL of each solvent, for 3–4 days each. The extraction scheme is illustrated in the process flow diagram depicted in FIG. 1.

The initial extract of paper was pooled from a number of different sources. In subsequent work, however, extracts from each colony were treated separately. Extracts were concentrated to dryness, then taken up in the extraction solvents for assays. Following application on the test substrate, solvent was thoroughly evaporated prior to all assays.

Bioassays. Preliminary feeding assays of the filter paper extracts were conducted by applying the extracts to fresh filter paper. These assays showed that the $CH_2Cl_2$ extracts from a variety of sources tended to deter feeding. The two more polar extracts either had no effect or were phagostimulatory in these paper feeding assays. Thus, the gross effect of the mixed fungal presence on the filter paper was deterrence, but potent phagostimulatory compounds lay within the fungus-filter paper matrix. The most polar (MeOH) phagostimulatory extracts from individual colony sources were used for subsequent thin layer chromatography (TLC) assays, as described below.

Gross phagostimulatory activity was assayed by supplying a known mass of extract in solvent to a block of cellulose TLC plate (0.1 mm cellulose thickness, E. Merck). A predetermined number of termites were then given access to the plate. Subterranean termites show no preference for the cellulose on untreated TLC plates (about 1×2 cm), lightly eating from only some plates in an apparently random manner. Where phagostimulatory material is present, the amount of cellulose consumed is a function of the intrinsic phagostimulatory nature of the compounds, number of termites, and extract dose.

TLC assays were performed by applying MeOH extracts from individual colony sources to the cellulose TLC plates using a microliter pipette or syringe, then presenting the plates to the termites. The extent of feeding stimulation was considered to correlate with cellulose consumed. After a designated time, the plates were removed and examined. TLC plates were either offered to a standard number of termites (typically 20 or 25) or set directly into colonies. Spurious, or unrepeatable positive responses were never observed in the TLC assays. The minimal feeding response elicited by untreated cellulose TLC plates allowed their use as controls for stimulant assays. While termites occasionally fed on control plates, the location of he feeding could not be associated with a site where either an otherwise nonactive fraction nor solvent control had been applied. No pattern of feeding on the untreated portions of assay plates was detected.

Figure 2A:
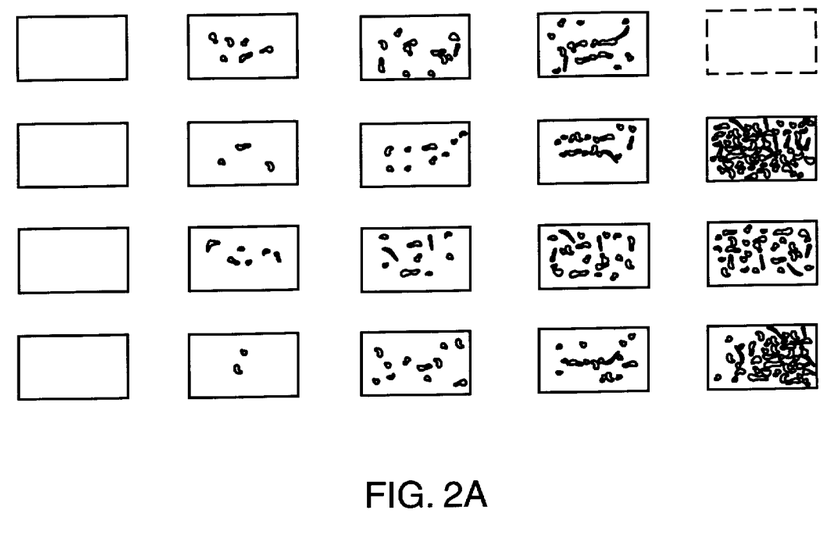
FIG. 2A shows a representation of the 1×2 cm cellulose thin layer chromatography (TLC) plates used to assess termite feeding activity in a dose-response assay of fungal extracts, as described in Example 1.
Figure 2B:
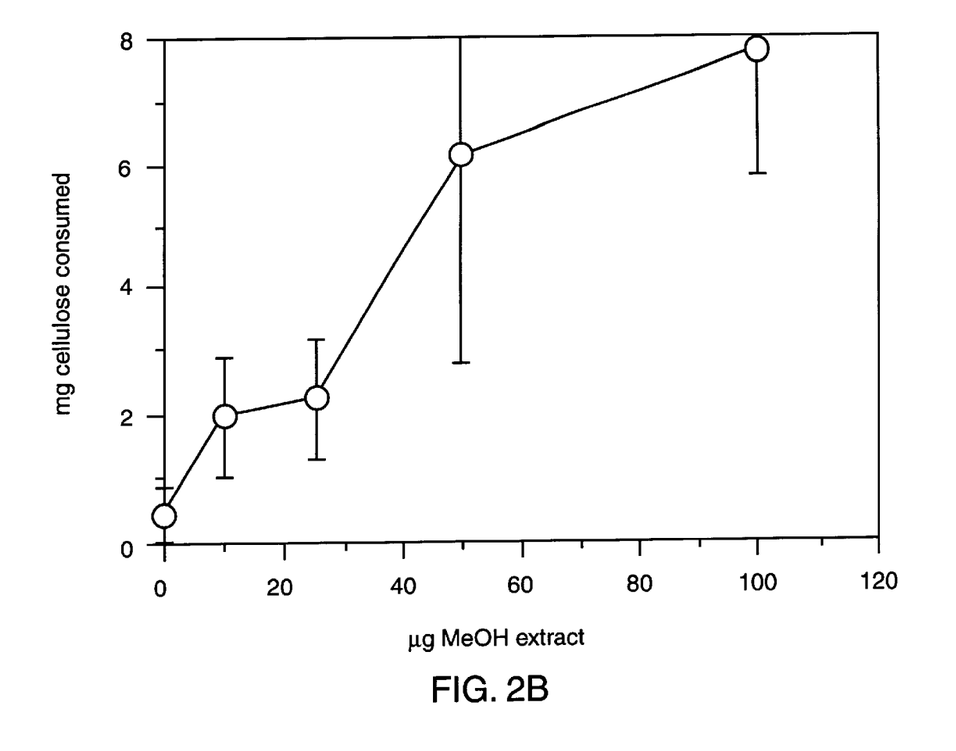
FIG. 2B depicts a graph illustrating the dose-dependent feeding response of the termites for the dose-response assay of extracts described in Example 1.

Assay results from the MeOH extracts from a series of fungus-colonized filter papers collected from several R. hesperus colonies are illustrated in FIGS. 2A and 2B. Feeding activity was measured by applying MeOH extracts to pre-weighed cellulose thin layer chromatography (TLC) plates, allowing the solvent to completely evaporate, then presenting each plate separately to groups of 25 third instar or older R. hesperus pseudergates (workers) for 72 hours, and weighing the plates following the assay.

FIG. 2A shows a representation of the 1×2 cm cellulose TLC plates used in this dose-response assay. In columns from left to right, 0 µg, 10 µg, 25 µg, 50 µg, and 100 µg of MeOH extract was applied to each of four separate plates. The phagostimulatory effect from each dose of extract is visible from the plates from the amount of cellulose consumed by the feeding termites, represented in the Figure by the darkened area on each plate.

FIG. 2B is a graph illustrating the dose-dependent feeding response of the termites. The data for this graph were obtained by comparing the weight of the plates before and after they were presented to the termites. The difference in weight of the plates was attributed to cellulose consumed by the termites. The graph shows that feeding increased with dose, indicating that the MeOH extract of the *R. hesperus*-associated fungal colonies is a feeding stimulant.

Example 2

Generality of Phagostimulatory Response for Different Colonies and Species of Reticulitermes The generality of the stimulatory response of both the Marin and Alameda methanolic extracts was tested against two different California *R. hesperus* colonies, and two congeneric termite species from eastern North America, *R. flavipes* and *R. Virginicus* (collected in Harrison County, Mississippi). Extracts and assays were performed substantially as described in Example 1. The results are represented in bar graph form in FIG. 3. When assayed at one dose level found to consistently elicit feeding for each extract, both the Alameda (25 $\mu$g) and Marin (50 $\mu$g) methanolic extracts were strongly preferred over controls for all colonies. The two extracts were consistently consumed more by the two Eastern species than by the California species, and the eastern species also exhibited a preference for the Alameda over the Marin extract. The California termites did not differentiate between these extracts. Thus, although these two extracts elicited feeding significantly above the control levels in the four colonies, the preference of the two eastern species for the Alameda extract is suggestive of differences in perception of the active compounds, the presence of different active compounds, or both. Overall, both *R. flavipes* and *R. virginicus* consumed more of the treatments than either *R. hesperus* colony.

Example 3

Fungal Subculturing and Isolation, Identification and Assays

The appearance of filter paper that has been left in laboratory colonies for weeks to months is indicative of microbial and fungal contamination. This paper assumes a mottled color of greys, pinks, and deeper reds. At this point termites appear to no longer feed on it. Isolation of the organisms from the paper was conducted using autoclaved pipette tips and glassware and distilled water. Infected filter paper was removed from two laboratory colonies derived from the Alameda colony filter paper that provided the active extracts described above. A 1 cm$^2$ piece of paper from each of these colonies, selected to be representative of the range of colors observed, was suspended in 3 mL of water and vortexed for 30 s. A 0.1 mL aliquot was transferred to 1 mL of water in a test tube, then four serial dilutions of the solution were prepared: From the first test tube, 0.1 mL was transferred to the second tube containing 1 mL of water. This tube was vortexed, then 0.1 mL was transferred to the third tube containing 1 mL of water, etc., for a total of five test tubes. Each of these tubes was vortexed 10 s, then 0.1 mL was transferred from each to a test tube (five total) containing 10 mL of melted malt-agar solution (2.5% malt extract, 1.8% agar) and the tubes were poured into five separate sterile petri dishes. Dishes were incubated at ambient laboratory temperature (about 20° C.) and as distinct organisms appeared, these were individually transferred to fresh malt-agar petri dishes and incubated, as above.

Cultures resulting from this procedure were allowed to expand to approximately 5 cm in diameter, then one-half of the culture (by area) was removed, taken through the same extraction sequence as the filter paper, and assayed for stimulatory activity, as described above in Example 1. Some of these mixed fungal cultures, but no bacterial isolates, from the Alameda colony were active. A single spore culture was prepared from the most active of these cultures, and extracts were prepared and assayed for stimulatory activity, as described for the colonized filter paper in Example 1. This active culture was identified as a zygomycete soil fungus, *Micromucor ramannianus,* based on morphological criteria (Arx, J. A. v. (1982). *On Mucoraceae s. str. and other families of the Mucorales.* Sydowia 35: 10–26) and the nucleotide sequence of the 18S ribosomal DNA gene.

Figure 4:
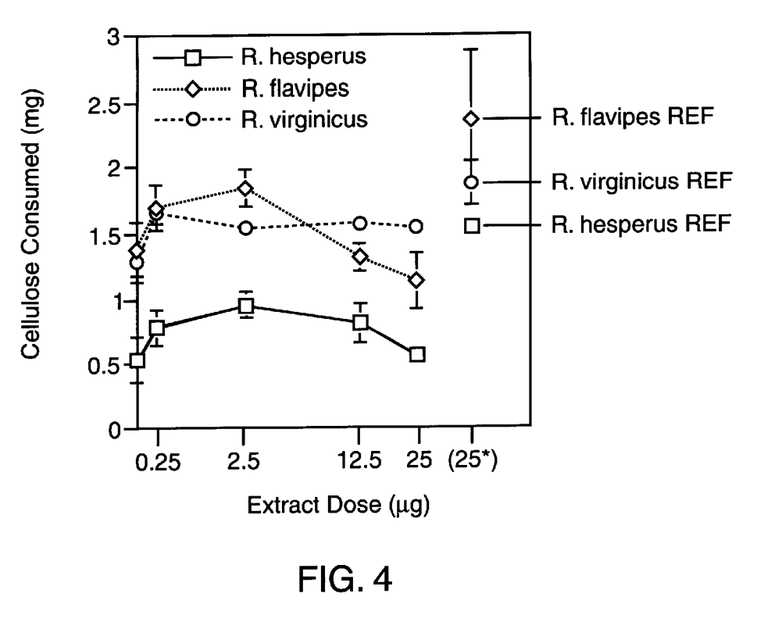
FIG. 4 shows dose-response relationships for *M. ramannianus* MeOH extract assayed against *R. hesperus, R. virginicus,* and *R. flavipes,* as described in Example 3.

FIG. 4 shows dose-response relationships for *M. ramannianus* MeOH extract assayed against *R. hesperus, R. virginicus,* and *R. flavipes* (each point on the graph represents a mean value for 6 replicates, +/− standard error). The *R. hesperus* termites used in this assay were from the colony source of the extract. Assay procedures are as described in Example 1, with each dose-colony combination represented by 6 replicates. The Alameda methanolic extract (25 $\mu$g, marked with a *) used in Example 2 was simultaneously assayed to provide a reference response for comparison with the earlier assays, also replicated 6 times for each colony. The doses are presented in a log$_{10}$ scale to show the detail of the response at low (0.25 and 2.5 $\mu$g) doses.

For both *R. hesperus* and *R. flavipes,* a regression of *M. ramannianus* MeOH extract dose on feeding response was statistically significant for a second order polynomial equation. For *R. virginicus,* all doses elicited greater feeding than control, but the response did not vary with dose. For the three species assayed, the stimulatory effect was elicited at the lowest level tested (0.25 $\mu$g) and saturated rapidly, achieving a maximum response at 2.5 $\mu$g.

The Alameda filter paper MeOH extract, assayed at 25 $\mu$g was significantly more stimulatory than the most active dose of the *M. ramannianus* MeOH extract for both *R. hesperus* and *R. flavipes.* It is therefore concluded that the stimulatory compounds in *M. ramannianus* represent an unknown proportion of the total pool of active fungal metabolites in the Alameda filter paper extract, which indicates that other fungi containing feeding stimulants are probably involved in the response. In light of the geographic diversity represented by the three Reticulitermes species assayed, the *M. ramannianus* MeOH extract shows a remarkable consistency in the responses elicited.

Example 4

*M. ramannianus* Stimulatory Assay

Figure 5:
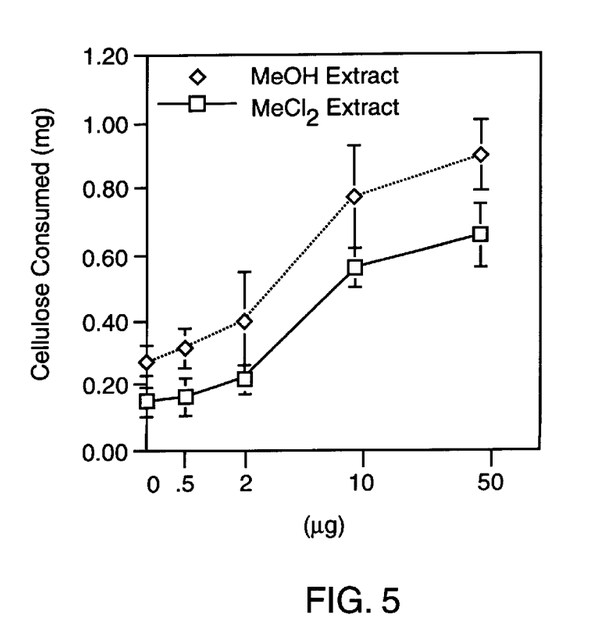
FIG. 5 shows the dose-response relationship for *M. ramannianus* MeOH (dashed line) and $CH_2Cl_2$ (solid line) extracts assayed against *R. hesperus* as described in Example 4.

In contrast to the deterrency associated with the Alameda filter paper CH$_2$Cl$_2$ extracts (as well as those from other mixed fungal sources), the *M. ramannianus* CH$_2$Cl$_2$ extract stimulated feeding by *R. hesperus* in choice assays. FIG. 5 shows the dose-response relationship for *M. ramannianus* MeOH (dashed line) and CH$_2$Cl$_2$ (solid line) extracts assayed against *R. hesperus* (complete dose series in each dish; 6 dishes; 50 termites per dish; each point on the graph represents a mean value for 6 replicates, +/− standard error). The assay termites were from the colony source of the fungal extract.

*Micromucor ramannianus* in culture synthesizes both non-polar and polar feeding stimulants with similar dose-response curves for subterranean termites. This zygomycete therefore synthesizes multiple feeding stimulant compounds for subterranean termites. The great polarity differences between the CH$_2$Cl$_2$— and MeOH-extractable compounds suggests that this fungus may be the source of stimulants possessing considerable structural variation.

Example 5

Chromatography

Phagostimulatory fractions of filter paper MeOH extracts taken from the Alameda and Marin colonies were subjected to several chromatographic steps. An initial solvent partition step (4:2:7 ethyl acetate:n-propanol:water (EPW)) retained activity in both solvent layers, and when the fractions were applied to cellulose TLC plates, developed in solvent, and the plates were set in termite colonies, feeding in different zones on the plates verified that the sources of activity had been partitioned into two chromatographically distinct groups. This step allowed further chromatography to be directed at a subset of the total active compounds.

Specific extracts were subjected to various combinations of RP-8, polyamide, and Sephadex G-10 and LH-20 chromatography. All fractions from each chromatography column were either assayed individually or pooled, based on their appearance on Silica gel TLC (developed in 65/35 Ethyl acetate/MeOH) when viewed under ultraviolet light (254 and 365 nm) and then sprayed with anisaldehyde-$H_2SO_4$ reagent and heated. This particular TLC spray reagent most easily revealed the glucose and other sugars in the MeOH extracts and allowed them to serve as readily detected internal markers for chromatography. Other spray reagents (including vanillin-$H_2SO_4$ and ceric sulfate-$H_2SO_4$) were also not as effective at visualizing many other constituents in the extracts. Due to differences between extracts from the two principal termite colony sources (Alameda and Marin), the chromatography sequence for each was treated separately. Activity of fractions was assessed as described above. Active fractions from the chromatography procedures described below were evaluated using RP-18 HPLC (Rainin gradient system, water/acetonitrile ($CH_3CN$), 25 cm×4.6 mm Vydac RP-18 column, UV detector set at 195 or 200 nm) and fractions were assayed as above.

Marin Colony Filter Paper Extracts

Sephadex G-10 Chromatography: A sample of the Marin filter paper MeOH extract (approximately 15 mg) was adsorbed onto Sephadex G-10 gel (Pharmacia), solvent was removed, the extract was loaded onto a 86×1 mm G-10 column in water and eluted at 1 mL/min. Fractions were concentrated to dryness under vacuum, then brought to 50 $\mu$L per fraction with MeOH. Column fractions were pooled based on their appearance on silica gel TLC when sprayed with anisaldehyde-$H_2SO_4$ reagent and heated. For adjacent pooled fractions, the total solvent volume represented the sum of the individual fractions. Approximately 5% by volume of each fraction was applied to cellulose TLC plates and placed directly into a termite colony. The pattern of active fractions that eluted from use of this chromatography gel was instructive for understanding the distribution of activity, but the use of G-10 Sephadex was later discontinued due to the co-elution of abundant saccharides, glucose in particular, with some of the active fractions. It was determined subsequently by use of polyamide S6 gel chromatography that the saccharides were not feeding stimulants for the termites. Thus the presence of these abundant sugars only complicated the chromatography. The Marin extract was not further chromatographed because of insufficient quantities.

Alameda Colony Filter Paper Extracts

RP-8 Chromatography: The upper layer from the EPW solvent partition of the Alameda MeOH extract (approximately 10 mg) was concentrated to dryness under vacuum, adsorbed onto RP-8 gel (E. Merck Si 60 RP-8, 40–63 $\mu$m) in water then loaded onto a 24×1.2 cm column in water. Fractions (f) were collected in 5 min increments, eluted with water (f 1–20), 80% water/MeOH (f 21–50), 50% MeOH/water (f 51–75), and MeOH (f 76–100). Fractions were recombined based on silica gel TLC patterns. Pooled fractions were assayed by concentrating to a standard volume based on 50 $\mu$L of MeOH per individual fraction and applying 1 $\mu$L aliquots of each fraction to a strip of cellulose TLC plate, and placing the plates in a termite colony.

Polyamide S6 Chromatography: Polyamide S6 chromatography gel (Reidel de Haen) was employed in an effort to remove saccharides (visualized using the anisaldehyde-$H_2SO_4$ spray reagent) from the early eluting (most polar) fractions in RP-8 chromatography. Simple saccharides, including glucose, are phagostimulants for many insects that have been examined (Bemays, E. A. and R. F. Chapman (1994). *Host-Plant Selection by Phytophagous Insects*. New York, Chapman and Hall). Because glucose may be a by-product of cellulose degradation (and thus a putative feeding cue for subterranean termites), it was necessary to unambiguously separate the active fractions from glucose and other sugars. Alameda MeOH extract (17 mg) was adsorbed onto polyamide resin, dried under vacuum, then loaded in water onto a 26×1 cm polyamide column. The column was eluted at 0.9 mL/min with water (f 1–20), 50% MeOH (f 20–50), 80% MeOH (f 51–84), 90% MeOH (f 85–110), and MeOH (f 111–120). Fractions were compared and visualized as above.

LH-20 Chromatography: The active fractions from polyamide S6 column chromatography were complex and contained multiple active compounds by HPLC analysis. In addition, the polyamide gel bled compounds into the column eluant that absorb strongly at the wavelengths (195 or 200 nm) used to monitor the HPLC. These contaminants also overlapped with active HPLC fractions. Since chromatography on RP-8 and polyamide consistently yielded several regions of active fractions, each of which was found by HPLC analysis to be a complex of active compounds, an additional chromatographic step that separates compounds on the basis of molecular weight appeared to offer a way to both remove contaminants from active compounds prior to HPLC analysis and to separate the complex clusters of compounds into their components. Therefore, all active fractions from four polyamide columns (approximately 50 mg of extract originally loaded) were re-combined and eluted through Sephadex LH-20 (Pharmacia) in isocratic MeOH (18×1.2 cm column). Fractions 1–8 were eluted in 2.5 min increments, fractions 9–60 at 1 min intervals. Silica gel TLC patterns directed pooling of fractions, which were assayed as above.

*Micromucor ramannianus* Agar Culture

Polyamide Chromatography: The MeOH extract of the combined mass of fungal mycelia of *M. ramannianus*, agar matrix, and malt extract, 10 mg (170 $\mu$L) was adsorbed onto polyamide gel; the MeOH was removed under vacuum and the gel with adsorbed extract was loaded onto the column. The extract was then eluted with water (20 mL), and MeOH (25 mL), to give four fractions. Each fraction was concentrated to dryness, solubilized in 500 $\mu$L MeOH, and 5 $\mu$L of each was applied to a strip of cellulose TLC plate and presented in a petri dish to 25 *R. hesperus* termites for 64 hours.

Figure 6:
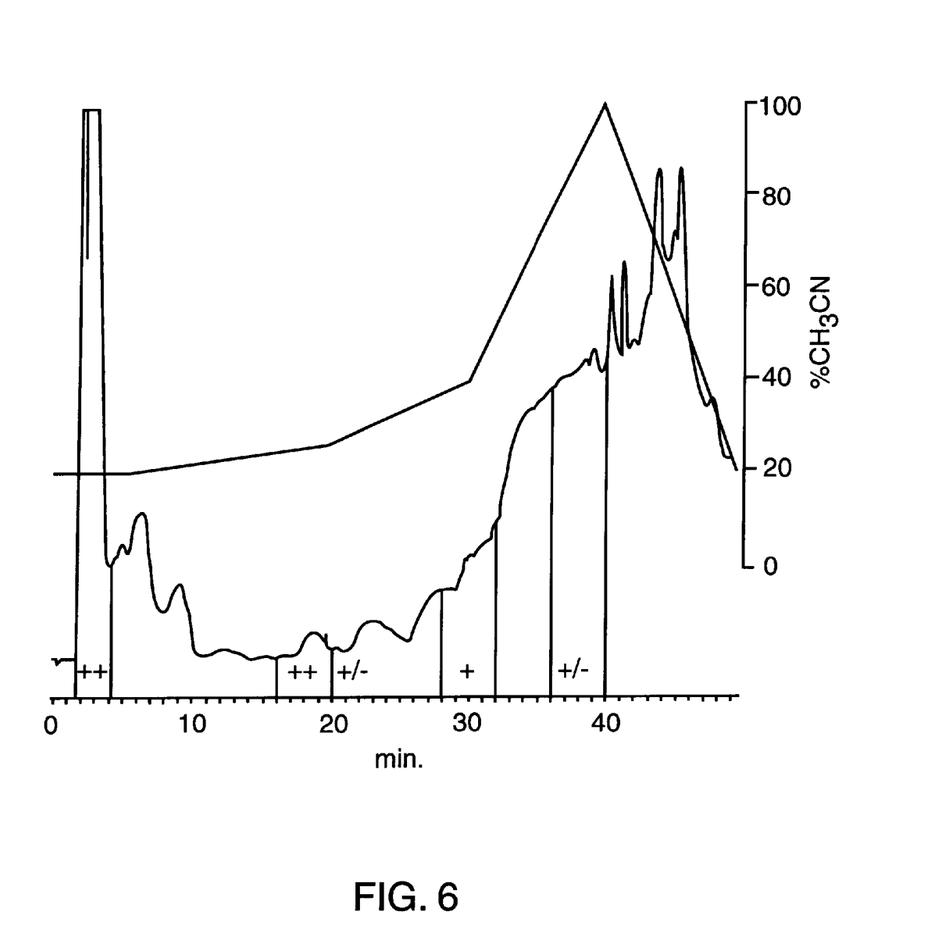
FIG. 6 depicts a RP-18 HPLC chromatogram of a fraction from a polyamide column separation of a *M. ramannianus* MeOH extract, as described in Example 5.

All the feeding stimulant activity in the *M. ramannianus* extract eluted from the polyamide column in fraction 4, 100% MeOH. Of the 10 mg loaded, the total weight of material in fraction 4 was 650 $\mu$g. The assay used 1% of the total, demonstrating that significant feeding was elicited with approximately 6–7 $\mu$g of extract. A sample of fraction 4 from the polyamide column was injected directly onto a RP-18 HPLC column (Vydac C-18 column, 25×4.6 cm) and eluted using a water/acetonitrile gradient. The chromatogram is illustrated in FIG. 6. From a total of 65 $\mu$g injected, twelve fractions were collected at four minute increments. Each fraction was applied to a cellulose TLC plate, and the fractions were assayed in three separate groups (20 R. hesperus each) for 24 hours. Three principle zones of activity were detected (at 200 nm), at 2–4, 16–20, and 28–32 minutes retention time, in addition to two regions with less, but still detectable activity, at 20–24 and 36–40 minutes. These results were replicated in four additional HPLC injections.

Implications from the Chromatographic Analyses

Interpretation of the various chromatograms and HPLC elution patterns suffered from the evident lack of strong chromophores in many active fractions. However, the results clearly indicated that there were multiple (chromatographically resolvable) active compounds within each extract tested. Even single open column fractions could have two or more sources of activity. This was markedly true for the isolated species, M. ramannianus. Accordingly, it appears that the phagostimulatory activity of the MeOH extract of the mixed fungal and single spore Micromucor ramannianus colonies has several chemically distinct contributors.

Example 6

Chemical Derivitization

Chemical derivitization was attempted on open column fractions derived from the Alameda filter paper extract. The goal was to prepare volatile derivatives for analysis by gas chromatography/mass spectrometry (GC/MS), but although the derivatized products were too complex to provide the expected mass spectra, the behavior of the derivatized extracts in bioassays yielded insights into the structure-activity relationship for the unknown phagostimulatory compounds.

Acetylation: A portion of an active fraction (approx. 50 $\mu$g) from RP-8 open column chromatography on the Alameda MeOH extract was stirred in a sealed glass vial with 100 $\mu$L of acetic anhydride (Supelco Co.) and 100 $\mu$L of dry pyridine for 3 h. The reaction mixture was washed with saturated NaCl, then partitioned between saturated aqueous $NaHCO_3$ and EtOAc, and the organic layer was concentrated. The product of the acetylation reaction was significantly less polar than the starting material by silica gel TLC analysis, indicating masking of hydroxyl moieties (and possibly carboxyls) by acetate.

After removal of solvent and volatile reagents under vacuum, the reaction mixture was assayed for feeding stimulatory activity on cellulose TLC. In cellulose TLC feeding assays against the Marin R. hesperus colony, no fractions were active. This loss of activity upon acetylation was seen for all active MeOH filter paper extracts assayed.

Silylation: These experiments were designed to replace the protons of the postulated hydroxyls with silyl ethers, using a trimethylsilyl derivatizing group. A pooled collection of active fractions from several Sephadex G-10 open columns on the Alameda MeOH extract (50 $\mu$g), was reacted with 100 $\mu$L of TriSil reagent (Pierce) for 3 h at 52° C. in a sealed glass reaction vessel. The volatile components of the reaction mixture were then removed by a vacuum pump. Conversion to products was assessed by silica gel TLC. The reaction mixture was fractionated using silica gel HPLC (Rainin 25 cm×4.6 mm column, isocratic hexane solvent, 200 nm detector), the volume of each fraction was taken to 10 $\mu$L with hexane (the silyl ethers were too nonpolar to be soluble in MeOH), and the total amount of each fraction was assayed on cellulose TLC in the Marin R. Hesperus termite colony.

The HPLC fractionation was then repeated for an identical silylation reaction (50 $\mu$g starting material). Each fraction of this second chromatography was concentrated to dryness, then treated with 200 $\mu$l of 0.01 M HCl for 1 hour. Hydrolysis had been attempted earlier with trifluoroacetic acid, but did not effectively remove the silyl ethers (determined by behavior on Si TLC). Silica gel TLC showed that the products of the acid treatment were significantly more polar than the silylated products. Each fraction was then concentrated to dryness with a vacuum pump, taken to 10 $\mu$L with MeOH and assayed as above.

By HPLC analysis, the trimethylsilyl derivatization reactions produced distinctly less polar compounds than the starting material, indicating masking of the hydroxyls (and possibly carboxyls) by silyl groups. The underivatized pooled G-10 active fraction material showed strong activity at 5 $\mu$L, in which cellulose from a TLC plate was removed to the glass backing. Assays verified that upon conversion to the silyl derivatives, all feeding stimulant activity was lost. When the silylated derivative (the product of reacting 50 $\mu$g of active material with TriSil reagent) was fractionated on silica gel HPLC, no fractions elicited feeding in cellulose TLC assays. Acid hydrolysis (0.01 M HCl) of all fractions from a duplicate HPLC fraction recovered feeding stimulant activity in several of the fractions.

The finding that the masking of the hydroxyls (and possibly carboxyls) by acetate and silyl groups destroys the activity of the feeding stimulant compounds constitutes strong evidence for a role of the hydroxyl moieties in the perception of these compounds by termites. The ability to convert the nonactive silyl ethers back to the active native compounds further indicates the importance of the hydroxyls and suggests a way to separate these complex fungal metabolite mixtures prior to analysis.

Example 7

Assays of M. ramannianus Extracts on Wood and Paper Substrates

The M. ramannianus methanolic extracts also stimulate feeding on filter paper and wood. For all assays described here, twenty R. hesperus were held in a small dish with the assay materials for each replicate.

On balsa wafers (0.1×2.2 cm), M. ramannianus methanolic extract applied at 2 parts per million (ppm; weight of applied extract as a proportion of the substrate weight) was preferred over control wafers (methanol only). By analysis of variance (4 replicates per treatment), 12 day assay:

| Treatment | Mean (mg) | Standard error | F ratio | p value |
| --- | --- | --- | --- | --- |
| Control | 1.18 | 0.23 | 15.69 | 0.0074 |
| 2 ppm | 2.41 | 0.21 | | |

Extracts were also tested on filter paper disks (Whatman No. 1, 2.5 cm) in two types of assays; choice (both control and extract-treated disks in the same dish, and no-choice (only one disk per assay dish). In the no-choice assay (8 replicates per treatment, 5 day assay), the 2 ppm M. ramannianus methanolic extract was consumed more than control. The results are presented as paper consumed per pair of extract and control disks: extract/extract+control. The expected mean value for this ratio is 0.5, if termites exhibit no preference for treatment or control. The actual value calculated is 0.789 (standard deviation 0.115), indicating a clear preference of the termites for the extract-treated paper disks.

A choice assay using a partially purified *M. ramannianus* methanolic extract prepared from a separate culture, presented at 400 ppm (8 replicates, 7 day assay) yielded similar results. In this case, the extract induced greater feeding than the control disks; the ratio of extract to extract+control was 0.695 (standard deviation 0.241).

Taken with the data from the cellulose TLC plate assays (Example 1), the assays described above demonstrate that *M. ramannianus* methanolic extracts induce feeding when applied to three types of cellulosic substrates.

CONCLUSION

The above examples provide evidence for feeding stimulant and deterrent activity elicited by extracts of subterranean termite-associated fungus-colonized filter paper and for feeding stimulant activity elicited by extracts of cultures of *Micromucor ramannianus*, a zygomycete fungus derived from this filter paper. Cellulose TLC assays demonstrated that a polar (MeOH) extract of the fungus-colonized filter paper was a feeding stimulant for the three subterranean termite species tested, *R. hesperus, R. virginicus,* and *R. flavipes*. This extract was shown to elicit feeding at levels apparently lying between about 5 and 10 µg, and possibly greater, in cellulose TLC assays. The *M. ramannianus* methanolic extracts also stimulated feeding on filter paper and wood. In contrast to the consistent deterrency associated with the filter paper $CH_2Cl_2$ extracts, the *M. ramannianus* $CH_2Cl_2$ extract stimulated feeding by *R. hesperus* in choice assays.

The presence of a complex of fungi on filter paper in laboratory termite colonies is an expected consequence of the artificial habitat created by maintaining termites and filter paper together in a warm and moist enclosure. The observation that colonization of the paper by an unspecified array of these organisms suppressed feeding by termites may not require any special explanation, other than that introduction of multiple compounds into any food source may alter its acceptability to a consumer. However, the presence of strong feeding stimulants in the extracts of the filter paper-fungus complex resulting from fungal colonization of this substrate was unanticipated. The possible existence of fungi that synthesize feeding stimulants was a surprise, since the gross behavioral effect of termite colonies to the filter paper was avoidance or deterrence, which masked the feeding stimulant effect. An experimental approach that sought evidence for feeding stimulant production among the collection of fungi from infected filter paper in a termite colony might miss this feeding stimulatory effect due to the net deterrent effect.

Figure 3:
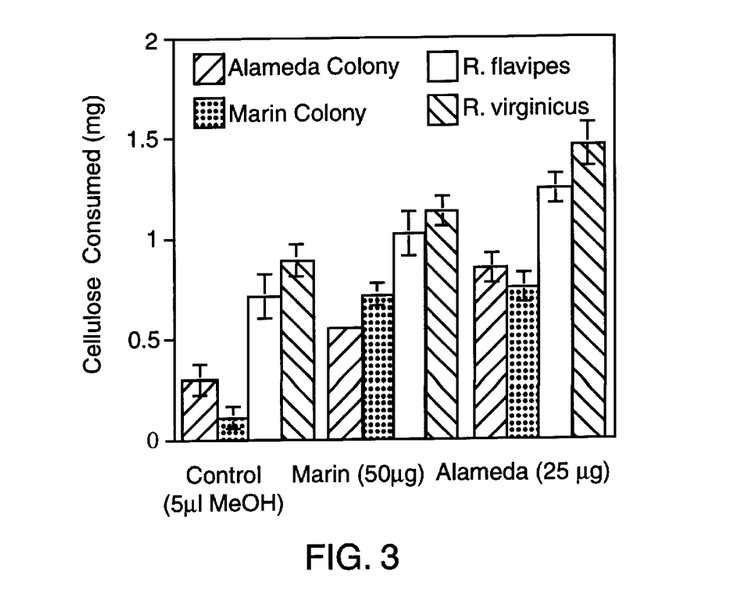
FIG. 3 depicts a bar graph illustrating the results of stimulatory response assays of both the Marin and Alameda methanolic extracts tested against two different California *R. hesperus* colonies and two congeneric termite species from eastern North America, *R. flavipes* and *R. virginicus* described in Example 2.

The overall feeding response elicited by the MeOH filter paper extracts appears to be generated by more than the one fungus identified in the examples above. Extracts of the malt-agar cultures of fungi from the Alameda fungus-infected filter paper revealed that other fungi (not currently identified) in addition to *M. ramannianus* elicited feeding in assays. The minimum quantity of MeOH extract of *M. ramannianus* (0.25 µL) required to elicit feeding on cellulose TLC was considerably lower than for the filter paper extracts. Yet, the feeding response to this single fungus extract declined rapidly, to the level of the control at 25 µg of extract, in one assay series (FIG. 4). The Alameda and Marin MeOH filter paper extracts were both strongly stimulatory in the range of about 25 to 50 µg (FIG. 3). This dose response disparity could be due to the presence of non-active materials in the filter paper extracts that add mass and thus dilute the active compounds, but the evidence for the presence of other fungi that produce feeding stimulants is consistent with multiple sources of activity. Chromatographic analysis revealed that the MeOH extract of *M. ramannianus* also contains multiple phagostimulatory compounds.

The finding that termite feeding stimulants in accordance with the present invention were active against three species of Reticulotermes from remote geographic locations in North America, together with previous findings that other chemical substances, such as trail following pheromones, are active across subterranean termite species (for example, Grace et al. (1988)) suggests that this broad cross-species stimulation may include other species and strains of Reticulotermes, and close relatives.

Thus, subterranean termite feeding stimulants have been isolated which may be incorporated into termiticide-treated bait-based systems and methods to selectively target and enhance control of subterranean termites.

It should also be noted that extractions performed to obtain phagostimulatory compositions in accordance with the present invention also produced compositions which deterred feeding of subterranean termites. These phagodeterrent compositions, obtained in the non-polar extract of subterranean termite-associated fungus-colonized filter paper, may also find useful application in termite control strategies, for example, by deterring subterranean termites from colonizing or feeding on particular substrates and structures.

Although the foregoing invention has been described in some detail for purposes of clarity of understanding, it will be apparent that certain changes and modifications may be practiced within the scope of the invention. It should be noted that there may be alternative ways of implementing both the processes and compositions of the present invention. Accordingly, the present embodiments are to be considered as illustrative and not restrictive, and the invention is not to be limited to the details given herein.

What is claimed is:

1. A phagostimulatory composition for termites, the composition comprising an extract from a medium colonized with zygomycete fungi, the extract extracted from the medium in a methanol fraction of a sequential methylene chloride ($CH_2CL_2$); 50% methanol (MeOH)/$CH_2Cl_2$; and MeOH extraction.

2. The composition of claim 1, wherein said zygomycete fungi coexist with subterranean termites.

3. The composition of claim 2, wherein said subterranean termites comprise species *Reticulitermes hesperus*.

4. The composition of claim 1, wherein said fungi comprise species *Micromucor ramannianus*.

5. The composition of claim 1, wherein said medium comprises filter paper.

6. The composition of claim 2, further comprising wherein said medium comprises malt-agar.

7. The composition of claim 6, wherein said fungi are isolated from said termites prior to extraction.

8. An apparatus for use in controlling a subterranean termite population, comprising:
    a termiticide-treated bait, wherein said bait comprises a composition in accordance with claim 1.

9. The apparatus of claim 8, wherein said bait further comprises a cellulose-based substrate for said termiticide and said composition.

10. The apparatus of claim 9, wherein said substrate comprises at least one of paper and wood.

11. The apparatus of claim 8, wherein said termiticide comprises hexaflumuron.

12. The apparatus of claim 8, further comprising a housing, said housing containing termiticide-treated bait, providing a coverable opening for placement and removal of said bait from said housing, and providing a second opening for giving termites access to said bait in said housing.

13. A method of controlling a subterranean termite population, comprising:

in a region of ground inhabited by subterranean termites, inserting into the ground a one or more termiticide-treated bait systems in accordance with claim 9.

14. A phagodeterrent composition for termites, the composition extracted from a medium colonized with zygomycete fungi, the composition extracted from the medium in non-polar extracts of the medium.

15. The composition of claim 14, wherein said zygomycete fungi coexist with subterranean termites.

16. The composition of claim 15, wherein said subterranean termites comprise species *Reticulitermes hesperus*.

17. The composition of claim 14, wherein said fungi comprise species *Micromucor ramannianus*.

18. The composition of claim 14, wherein said medium comprises filter paper.

19. The composition of claim 14, wherein said non-polar extract comprises $CH_2Cl_2$.

* * * * *